United States Patent [19]

Tanguy

[11] Patent Number: 4,781,181

[45] Date of Patent: Nov. 1, 1988

[54] BORING SENSOR FOR INTRAMEDULLARY NAIL AND CORRESPONDING INTRAMEDULLARY NAIL

[75] Inventor: Christian Tanguy, Choisy-Le-Roi, France

[73] Assignee: Zimmer, S.A., Vitry-Sur-Seine, France

[21] Appl. No.: 900,459

[22] Filed: Aug. 26, 1986

[30] Foreign Application Priority Data

Aug. 27, 1985 [FR] France ................. 85 12777
Aug. 13, 1986 [FR] France ................. 86 11720

[51] Int. Cl.$^4$ ............................................. A61F 5/04
[52] U.S. Cl. ................................................ 128/92 YZ
[58] Field of Search ....... 128/92 YY, 92 YZ, 92 YW, 128/92 YT, 92 VD, 92 V

[56] References Cited

U.S. PATENT DOCUMENTS

| 4,016,874 | 4/1977 | Maffei et al. | 128/92 YZ |
| 4,103,683 | 8/1978 | Neufeld | 128/92 YZ |
| 4,281,649 | 8/1981 | Derweduwen | 128/92 YZ |
| 4,399,813 | 8/1983 | Barber | 128/92 VD |
| 4,612,922 | 9/1986 | Barber | 128/92 VD |
| 4,621,628 | 11/1986 | Brudermann | 128/92 VD |
| 4,622,959 | 11/1986 | Marcus | 128/92 VD |

Primary Examiner—Robert A. Hafer
Assistant Examiner—Michael Brown
Attorney, Agent, or Firm—Burgess, Ryan and Wayne

[57] ABSTRACT

The present invention concerns a guiding, positioning and boring sensor, comprising a flexible shaft mounted in rotation and axially displaceable in a flexible sheath presenting an external diameter substantially smaller than the minimum diameter of the transverse cross section of the cavity defined in the intramedullary nail, the flexible shaft bearing at a distal end a boring head and at its proximal end a connecting device to a rotary motor whereas the sheath is integral through its distal end to a guiding and positioning unit provided with an internal passage that is connected to the bore of the sheath and presents a transverse cross-section identical to that of the bore.

19 Claims, 6 Drawing Sheets

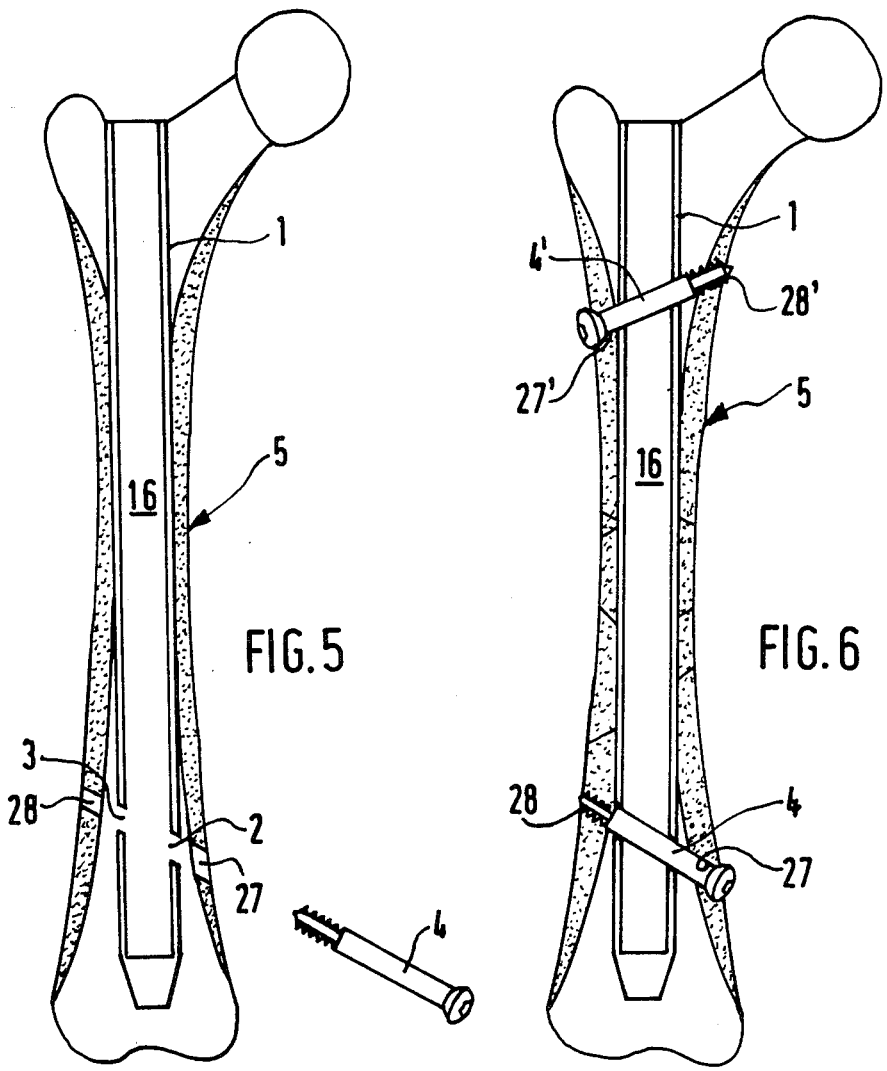

4,781,181

BORING SENSOR FOR INTRAMEDULLARY NAIL AND CORRESPONDING INTRAMEDULLARY NAIL

BACKGROUND OF THE INVENTION

1. Field of the Invention

The present invention concerns a guiding, positioning and boring sensor device, adapted to be utilized for securing an intramedullary nail prior to its placing within the medullary canal or cavity of a damaged bone. It also concerns an intramedullary nail to be secured through utilizing this sensor.

The invention concerns more particularly a locking intramedullary nail, i.e. intended to be secured with respect to the bone through at least one screw crossing through two facing and aligned screw holes, previously provided in the nail and also passing through the adjacent corticals on either side of the nail, whereas the above-mentioned fixation device is intended to allow the placing in position of such a screw.

The intramedullary nail considered in the present description is of the type constituted by a quasi-tubular rigid element, especially metallic, that presents a constant non-circular cross-section on at least the major part of the length of the nail. As a general rule, nails of this type do not have a continuous peripheral wall, but define a longitudinal slot extending along the whole length of the nail.

2. Description of the Prior Art

The conventional widespread method utilized up to now for placing, or implanting, such an intramedullary nail, especially in distal position, consists essentially in boring, at one end called proximal end of the bone to be treated, an opening offering longitudinal access to the medullary canal, for introducing the nail within through this opening, by longitudinally displacing within the canal until it reaches the required depth of penetration, in marking the site and the position of the screw holes of the nail, in boring holes in the two opposite cortical zones adjacent to the said screw holes of the fixation holes aligned with precision upon the screw holes, in introducing a screw into these screw and fixation holes and in securing it through screwing in the cortical zone receiving the tip (or the fore end) of the screw, the fixation hole provided in this cortical zone presenting with this aim a diameter smaller than the diameter of the diameter of the top of the thread of the screw.

Although this is the only method that can be applied by utilizing currently available surgical equipment, it presents a serious drawback in that the marking of the sites at which the bone must be bored transversally in order to provide the above-mentioned fixation holes in exact alignment with the screw holes of the nail previously put in place, is an extremely delicate operation. In most cases, the surgeon has to use, for this purpose, the radioscopy technique, utilizing brightness amplifiers, frame finders, etc. These complicate and prolong the surgeon's labour, while extending the time period during which the patient is maintained under anaesthesia, and above all exposes the surgeon and the patient to an undue amount of X-ray radiation.

SUMMARY OF THE INVENTION

The aim of the present invention is to propose a device, especially a guiding, positioning and boring sensor allowing to overcome the drawbacks described hereinabove during its utilization for the fixation of a suitable intramedullary nail, due to the possibility that it proposes applying a novel method of fixation without needing to tedious procedures requiring skill and time such as radioscopy or analogue techniques.

In order to achieve this aim, the boring sensor intended to be housed within an intramedullary tubular nail from an accessible end of the nail in order to drill a passage or a bore in the cortical wall of a bone that bears the nail, is characterized in that it comprises a guiding and positioning unit which is guided and axially movable in the internal recess of the nail and which bears a sheath internally crossed through by a flexible shaft bearing at its distal end a boring head and at its proximal end means for coupling to a rotary motor and in that said sheath issues at its proximal end axially from the internal recess of the nail and respectively at its distal end, laterally in the direction of the internal wall of the nail by a distal orifice situated opposite a screw hole provided in the wall of the nail, the said unit furthermore comprising positioning means adapted to cooperate with the complementary positioning means of the intramedullary nail so as to set in position the proximal outlet of the sheath opposite the corresponding screw hole.

The boring sensor can comprise a flexible shaft mounted in rotation and axially displaceable within a flexible sheath presenting an external diameter substantially smaller than the minimum diameter of the transversal cross-section of the canal defined within the intramedullary nail, the said flexible shaft bearing at its distal end a boring head and at its proximal end means for coupling to a rotary motor, while the said sheath is integral at its distal end with a guiding and positioning unit provided with an internal passage that is connected to the bore of the said sheath and presents a cross-section identical to that of said bore, the said passage comprising a first portion of passage aligned upon the bore of the sheath and a second passage portion forming, with the said first portion, an obtuse angle and issuing upon the surface of the said guiding unit through an opening adapted to be aligned upon an inlet screw hole provided in the wall of the intramedullary nail considered, the said unit comprising, furthermore, positioning means intended to cooperate with complementary positioning means of the intramedullary nail; the external outline of this unit being complementary to the internal outline of the intramedullary nail in such a way as to be able to be introduced within its proximal end and to be displaced longitudinally through sliding within the said nail, while being rendered immovable in rotation.

Advantageously, the said means for positioning the guiding unit comprise a ball mounted so as to be moveable within a housing or recess provided within said unit according to an axis substantially transversal to the sliding direction of the said unit in the nail and angularly shifted with respect to the said passage opening, this ball urged by a spring placed within the said recess and having a tendency to maintain the ball in a position in which it protrudes from the external surface of the said unit in such a way as to be able to cooperate with the said complementary positioning means of the nail that are constituted by a recess provided in the wall of the nail in a position determined with respect to the inlet screw hole of the nail, the arrangement being such that the engagement of the ball within the positioning recess is produced when the passage opening is aligned upon the inlet screw hole of the nail.

In one preferred embodiment, the positioning recess is constituted by a positioning hole crossing through the nail wall.

Both the recess and the passage opening are preferably disposed in the zones of the said unit that are in direct contact with the internal wall of the nail when the said unit is introduced into this nail.

Advantageously, the guiding unit is provided with a handling rod extending in the same general direction as the flexible sheath and provided with a gripping handle that extends beyond the proximal end of the said nail for all longitudinal positions of the said guiding unit within the nail.

The hollow nail according to the invention with an internal cavity that is adapted to be utilized in combination with the guiding sensor defined herein-above presents a constant non-circular transversal outline on the major portion of its length and is provided, at least in the distal portion of its wall, with at least one inlet screw hole and at least one outlet screw hole aligned according to common axis upon the inlet screw hole, wherein the essential feature of this nail is that the said common axis of alignment of the inlet and outlet screw holes is inclined with respect to the longitudinal median axis of the said nail under an angle equal to the slope angle of the second portion of passage of the said guiding unit with respect to the first portion of this passage, and wherein a positioning recess adapted to cooperate with the positioning ball of the said unit is provided in the wall of the nail, in a portion of said nail that is adapted to enter into direct contact with the surface of the said unit when said unit is brought, through sliding in the nail, into the zone of this portion of the wall.

Preferably, the said positioning cavity is constituted by a positioning hole crossing through the nail wall.

The axis of the above-mentioned positioning hole is situated in the same plane as the common axis of the said inlet and outlet screw holes.

In this case, the diameter of the positioning hole is, preferably, substantially greater than that of the outlet screw hole.

In one alternative, this axis of the positioning hole is situated in a plane that is angularly shifted with respect to the plane containing the common axis of the inlet and outlet screw holes.

The transversal cross-section of the hollow intramedullary nail presents a plurality of lobes, whereas the guiding unit presents an external outline matching at least one of the lobes.

Preferably, there are three lobes defined by the transversal section of the nail and the external outline of the said guiding unit matches two of these lobes.

The guiding unit is provided with a rigid handling rod, one end of which protudes, for any given position of the said unit in the intramedullary nail, from the proximal end of the said unit.

It becomes apparent from the preceding description that, due to the present invention, it is henceforth possible to proceed with the putting in place of fixation screws for an intramedullary nail in the medullary canal involved by boring the corticals through the internal route at desired sites, the boring tool being positioned with total accuracy, without their being need for conventional marking, positioning and boring procedures under radioscopic control.

BRIEF DESCRIPTION OF THE DRAWINGS

The invention will become more apparent from reading the following detailed description, given with reference to the appended drawings, it being well understood that said description and the drawings are given solely by way of non-limitative illustration.

FIG. 5 shows in longitudinal cross-section, an intramedullary nail according to the invention, put into place in a femur in which have been made several holes intended to receive a screw;

FIG. 6 is a cross-section analogue to that of FIG. 5 and shows an intramedullary nail according to the invention put in place in a femur in which it is secured by two screws;

DETAILED DESCRIPTION OF THE INVENTION

Figure 1:
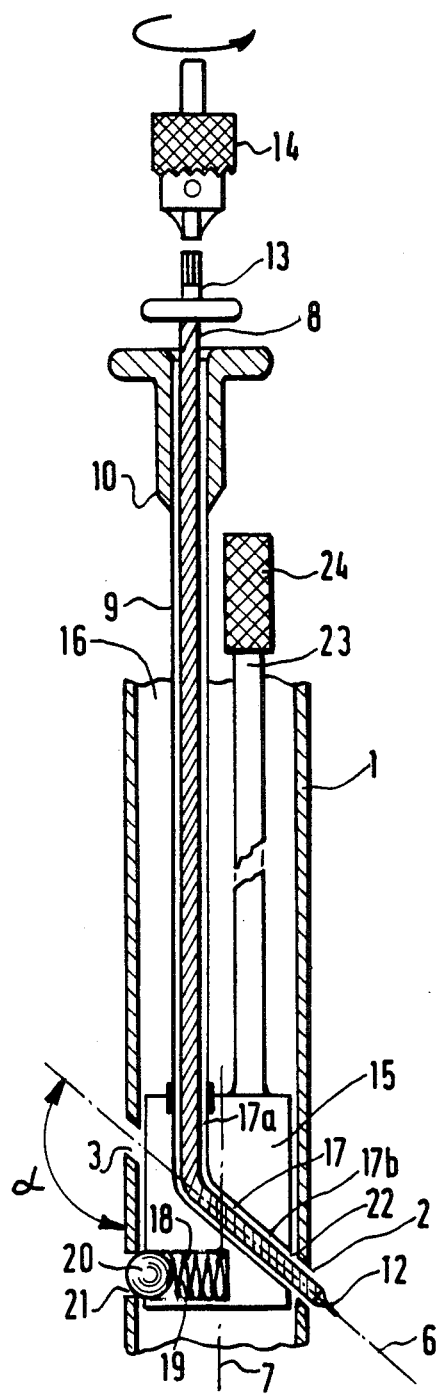
FIG. 1 represents schematically, in a longitudinal cross-section, one embodiment of the surgical equipment according to the invention.
Figure 2:
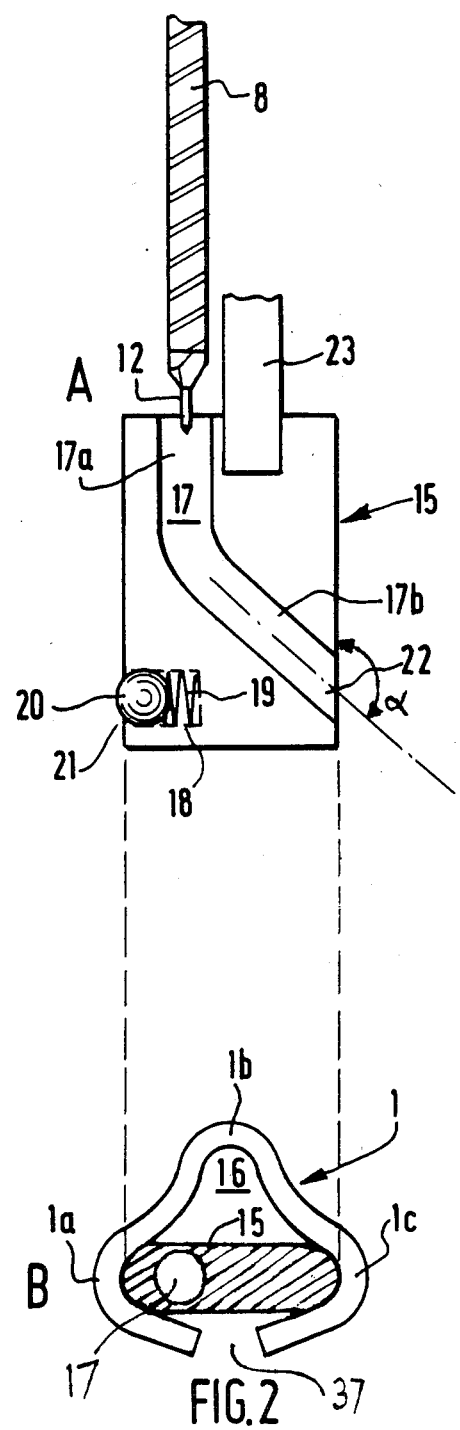
FIG. 2 shows on the one hand, in A, also in a longitudinal cross-section, the guiding unit and, on the other hand, in B, a transversal cross-section of the same unit disposed inside the intramedullary nail.

The equipment according to the invention comprises an intramedullary nail 1, represented in longitudinal cross-section in FIG. 1. In the present embodiment, the non-circular transversal cross-section, of nail 1 defines three lobes 1a, 1b, 1c disposed substantially according to an isosceles triangle, as well as shown by part B of FIG. 2. The nail 1 is provided with two screw holes 2 and 3 foreseen respectively in the lobes 1c and 1a and intended to receive a screw 4 (FIG. 5) for securing the nail in the medullary canal of a bone, for example, a femur 5. This screw is intended to be introduced through hole 2, or inlet hole, and to thereafter cross through, by its fore end (or tip) the hole 3, or outlet hole. For reasons that will appear evident from the following description, the inlet and outlet screw holes 2, 3, that are aligned with each other, are disposed according to a geometrically common axis 6, that forms an obtuse angle alpha with the median longitudinal geometric axis 7 of the nail 1, and consequently with a generatrix of its wall. It is appropriate to note that the outline (especially the internal outline) of the hollow nail 1 is constant along the whole length of a substantially rectilinear portion of the nail, and that the present description refers to this rectilinear portion having a constant outline. The nail according to the present embodiment comprises, in a manner widely known per se, a longitudinal slot 37 (FIG. 2) extending along practically the whole of the length of the nail.

The equipment according to the invention comprises, furthermore, a flexible shaft 8 mounted, in a manner known per se, in rotation in a flexible tubular sheath 9 provided at one of its ends (referred to as the "proximal end") with a tubular handle 10 integral with the said sheath and intended to help the introduction of the flexible shaft 8 in said sheath, as well as its withdrawal.

The flexible shaft 8 bears on one of its ends (referred to hereinbelow as "distal end") a drilling or boring tool, such as a bit 12 of a type currently used in surgery for boring bones. At its other end, or the proximal end, the flexible shaft 8 is provided with connecting means 13 to a rotary motor 14.

The sheath 9 is fixed by its opposite or distal end to the handle 10, onto a guiding unit 15 presenting an outline such that it can be introduced into a cavity defined by the nail 1 and that it can be displaced there by means of sliding in the direction of the axis 7 of the nail, while being rendered immovable in rotation with respect to the nail. With this purpose, the unit 15 matches, in the present example, the internal concave outline of the two opposite lobes 1a and 1c of the nail 1, as it will appear in particular from the transversal cross-section represented in B on FIG. 2.

The guiding unit 15 is provided with an internal passage 17 the transversal cross-section of which corresponds to that of the bore or passage defined inside the sheath 9 and acting as housing of the flexible shaft 8. The connection between the sheath 9 and the unit 15 is such that the passage 17 is connected to the above-mentioned bore or housing, as will be apparent from FIG. 1. A first portion, or inlet portion 17a, of the passage 17 is aligned upon the terminal distal portion of the sheath 9 and thus extends substantially parallel to the longitudinal median axis 7 of the nail 1 when the unit 15 is placed within the cavity or recess 16 of the nail 1, whereas a second portion, or distal portion 17b of the said passage that issues at output opening 22, forms with the proximal portion 17a (and, consequently, with the axis 7 or with the generating line of the nail 1) an obtuse angle equal to the angle alpha mentioned herein-above. The value of this angle is selected by taking into account in particular the characteristics of the flexible transmission constituted by the shaft 8 and the sheath 9, i.e. that it must not be smaller than a limit value from which a satisfactory transmission of the rotation torque between the motor 14 and the bit 12 would no longer be ensured.

The guiding unit 15 is provided with a blind cylindrical housing 18 extending perpendicularly to the axis 7 (with reference to the unit 15 introduced into the nail 1) and containing a helical spring 19 coaxial to the said housing, that urges towards the outside of the unit 15 a positioning ball 20 able to be displaced within the housing 18 in the direction of its geometric axis, and to protude, under the action of the spring 20, from the housing opening without, however, being able to escape therefrom. The ball cooperates by snapping with a positioning recess formed in the present example by a hole 21 provided in the wall of the nail 1 in the lobe opposite that which presents by the inlet screw hole 2. The site of the positioning hole 21 is selected so that—taking into account the disposition of the guiding unit—the ball 20 penetrates partially within the hole 21 when the outlet orifice or opening 22 of the passage 17 is aligned on the inlet screw hole 2 of the nail 1. In the embodiment represented, the positioning hole 21 and the outlet screw hole 3 have their respective centers placed on a common generatrix of the wall of the nail 1. Consequently, in order to prevent positioning errors, the positioning hole 21 is provided with a diameter substantially greater than that of the outlet screw hole 3, thereby bringing about utilization of a ball 20 of a relatively large diameter, so that there is no risk that, during the placing in position of the unit 15, the ball produces a snapping effect in the screw hole 3, which could thus be wrongly interpreted as indicating that the unit 15 has reached the desired position in the recess 16 of the nail.

In order to facilitate handling, the unit 15 is provided with a solid rod 23 which extends in the same general direction as the sheath 9 and provided, at its free end, with a gripping handle 24 that extends beyond the proximal end of the nail 1 for any given position of the unit 15 in said nail.

Figure 4:
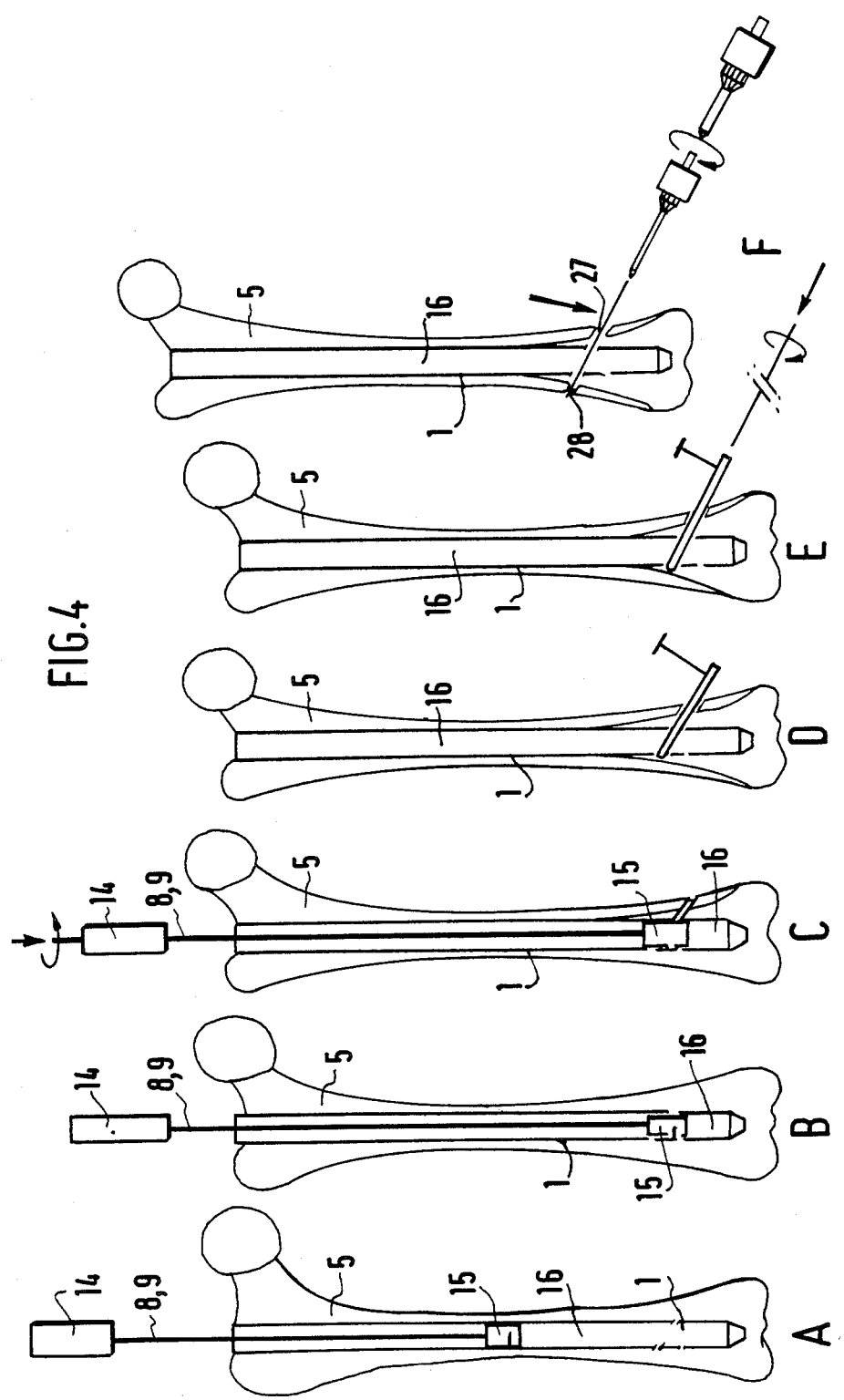
FIG. 4 illustrates in the form of schematic longitudinal cross-section A to F different successive steps of the utilization of the equipment according to the invention for the consolidation of a femur.

Diagrams A to F of FIG. 4 represent different successive steps of utilization of the equipment according to the invention for consolidation of a femur.

After the putting in place of the nail 1 in the medullary cavity of the femur 5, the guiding unit 15 is introduced in the recess 16 of the nail 1 (FIG. 4A) by means of rod 23. When the engagement of the ball 20 in the positioning hole 21 of the nail indicates that the unit 15 has reached the desired position, in which the orifice 22 of the passage 17 is aligned with the outlet screw hole 2 of the nail (FIG. 4B), the flexible shaft 8 is caused to rotate by means of a motor 14 and this shaft is caused to advance the bit 12 through the screw hole 2 and to bore in the adjacent cortical a hole that will thus be perfectly aligned on the screw hole 2.

Thereafter, a boring guide is placed in a manner known per se through external route, (FIG. 4C) thereby allowing the application of a Kirchner pin passing through the nail and the two cortical zones on either side of said nail (FIGS. 4D and E).

By utilizing this pin, acting as a guide rod, a boring operation is thus carried out, in 27, on the cortical adjacent to the outlet screw hole 3 at an internal diameter equal to the diameter of the bottom of the thread of screw 4 (FIG. 5) to be put in place, whereas the other cortical is bored in 28 at the diameter of the top of the thread of this screw, these two successive boring operations being carried out by utilizing two drills schematically indicated on FIG. 4F.

FIG. 5 shows the femur 5 provided with the intramedullary nail 1, after boring of the cortical zones in 27 and 28, as well as the screw 4, prior to putting in place said screw and FIG. 6 is a similar view to that represented in FIG. 5, showing, in its lower portion, the femur 5, the nail 1 and the screw 4 put in place definitively.

Figure 3:
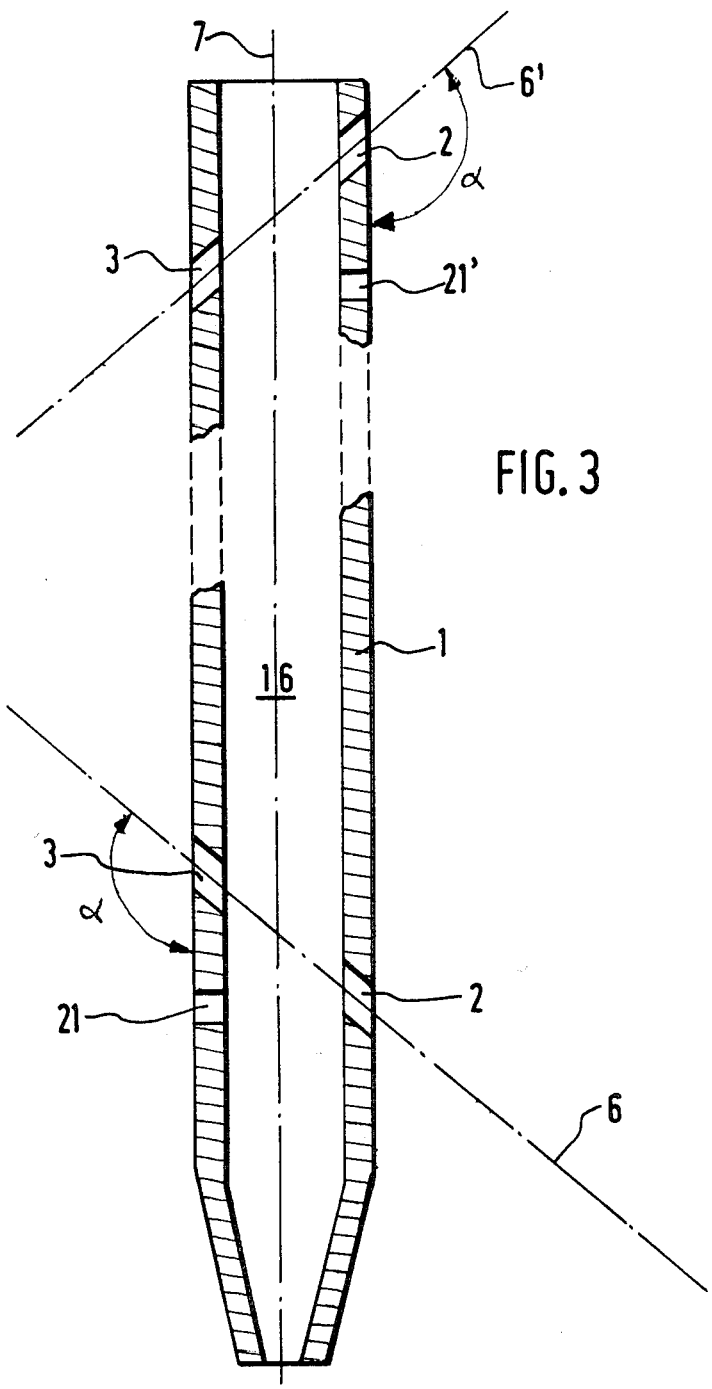
FIG. 3 is a longitudinal cross-section of a portion of the intramedullary nail according to the invention and shows more particularly the different dispositions of the screw and positioning holes.

By introducing the guiding unit 15 into the recess 16 of the nail in a position shifted by 180° with respect to that involved in the following description, it is possible, as diagrammatically indicated by the upper portion of FIG. 3, to bore the bone by using the flexible shaft 8 and the bit 12 on the opposite side to that presently involved, provided, of course, that the disposition of the screw holes and positioning holes is also shifted by 180°. This is symbolized by the use, on the upper portion of FIG. 6, of the same numeral references as those utilized on the previous drawings and in a lower portion of FIG. 6, but provided with a "prime" (') sign. It will thus be understood that in these conditions the common axis 6' is also inclined at a same angle alpha with respect to the median axis 7 of the nail, but in the opposite direction with respect to the disposition described hereinabove.

It is thus possible, where necessary, to fix a single intramedullary nail 1 by means of two screws 4 and 4' housed respectively in the holes 27, 28 and 27', 28' and bent at equal angles (alpha), but in opposite directions, as represented in FIG. 6.

According to the embodiment described hereinabove, the guiding of the flexible shaft is thus ensured in such a way as to allow its rotation at a relatively high speed, but the boring transversally in the cortical of the bones has proved to be very difficult to perform since the boring head tends to be deviated by the oblique application of bit 12 on the internal surface of the hard wall of the bone.

According to another embodiment of the boring sensor and intramedullary nail allowing to eliminate these latter drawbacks while avoiding the need of time-consuming and dangerous procedures such as radioscopy of the bone during drilling, the sheath presents, in the vicinity of the guiding unit a rigid wall that issues opposite the internal wall of the nail in a position substantially perpendicular to that wall. The sheath presents, along its entire length, a rigid wall inside of which is axially provided the flexible shaft in order to control the feed and withdrawal movements of the boring head.

The flexible shaft comprises a flexible sheath, rigid or quasi rigid in compression, for example a metallic sheath, axially movable and inside of which is mounted a rotary flexible rod presenting a great resistance to flexion-rotation stresses for example in nylon gut, and bearing respectively at its distal end, a boring head intended to bore the cortical of the bone from the boring passage provided in the wall of the nail and, at its proximal end, a driving in rotation head.

According to another embodiment of the boring sensor, the boring head presents a bearing surface allowing the flexible sheath to push the boring head in order to induce its moving forward during its driving in rotation by the flexible rod, without exerting any axial effort on this flexible rod. The boring head and/or the driving in rotation head is, preferably, secured by crimping onto the flexible rod.

The intramedullary nail with an internal cavity or recess, adapted to receive a boring sensor according to the invention and presenting a substantially constant transversal outline having a generally tubular form and aligned inlet and outlet screw holes or pins, its distal end being slightly pointed while its distal end is provided with at least one screw passage inclined with respect to the longitudinal median axis of the said nail, is characterized according to this latter embodiment of the invention in that it comprises at its distal end, before the pointed zone, on the one hand at least two pairs of holes or passages aligned transversally with respect to the axis of the nail for the passage of fixation screws of the bone crossing through the nail and, on the other hand, positioning and securing means for the boring sensor device, each corresponding to one of the pairs of holes.

According to one advantageous embodiment, the positioning means are constituted by a specific hole, different from those of the pairs of holes and intended to receive a protruding ball or a projecting rod borne by the guiding sensor.

Figure 7:
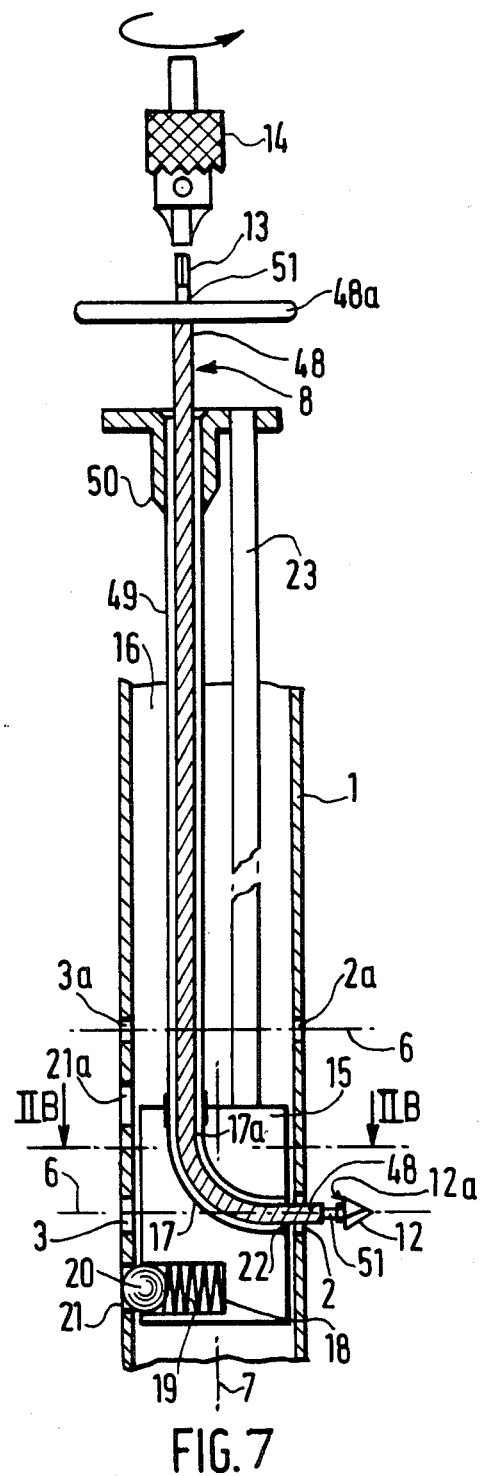
FIG. 7 represents schematically, in longitudinal cross-section, another embodiment of the boring sensor according to the invention, placed in an intramedullary nail in order to radially drill a bone.
Figure 8:
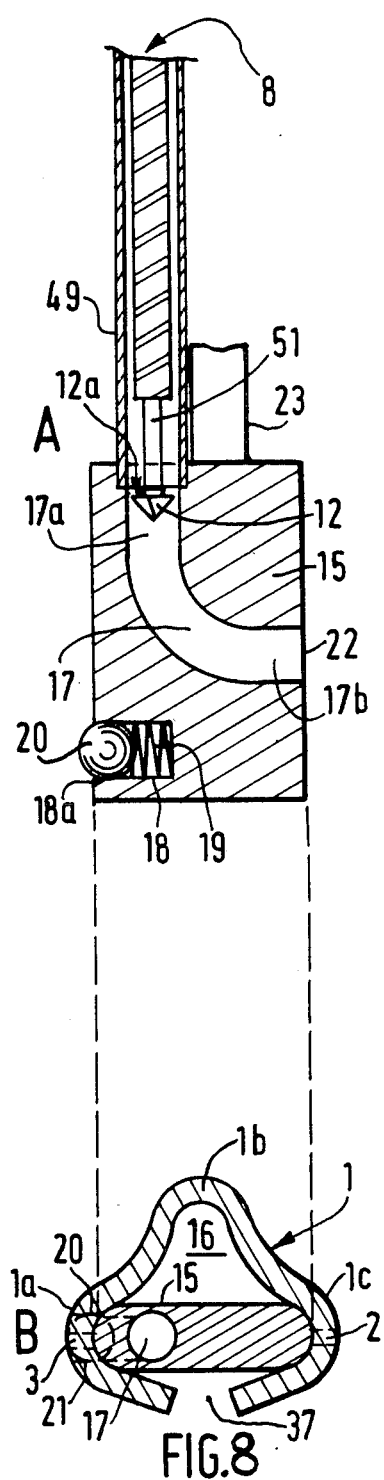
FIG. 8 shows, on the one hand in A, also in longitudinal cross-section and on a larger scale, the guiding unit of the sensor and, on the other hand in B, in traversal cross-section on a larger scale, along the line IIB of FIG. 7, of the same unit disposed inside the intramedullary nail.
Figure 9:
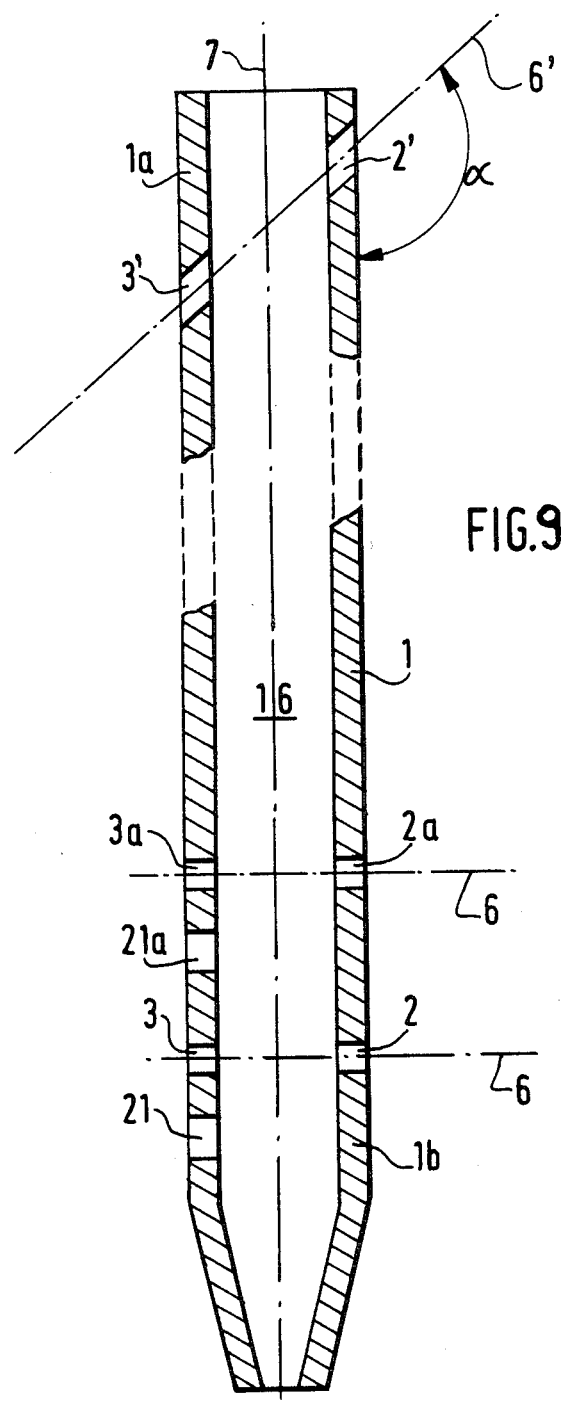
FIG. 9 is a longitudinal cross-section of a portion of the intramedullary nail according to the invention and shows, more particularly, different arrangements of the screw and positioning holes provided in this nail.

In the embodiment according to FIGS. 7 to 9, where the elements identical to those of FIGS. 1 to 6 have been designated with the same reference numerals, the sensor according to the invention comprises a flexible shaft 8 rotary mounted in rotation in a rigid tubular sheath 49 provided, at one of its ends (called herein proximal end) with a tubular handle 50 integral with the sheath 49 and adapted to facilitate the introduction of the flexible shaft into the said sheath as well as its withdrawal.

The flexible shaft 8 is constituted by a flexible sheath 48, rigid or quasi rigid in compression, inside which is rotary mounted in rotation a flexible rod 51, highly resistant to flexion and constituted for example by a thick nylon thread or gut or core and which bears at one of its ends (called herein-after distal end) a boring or drilling tool such as a bit 12 of the type commonly used in surgery for boring a bone. At its other end, or proximal end, the flexible rod 51 is provided with coupling means 13 for example a sleeve having a square section, for connecting it to a rotary motor 14. The bit 12 and the sleeve 13 forming the driving in rotation head are preferably crimped on the flexible rod 51.

The sheath 49 is secured, by its end opposite to the handle 50 or distal end, to a guiding unit or block 15 presenting an outline so that it may be introduced into recess 16 defined inside the nail 1 and may be slidably displaced in the direction of axis 7 of the nail while being immobilized in rotation with respect thereto. With this purpose, the unit 15 is complementary, in the present example, to the concave internal outline of the two opposed lobes 1a and 1c of the nail 1 as well as it appears, especially, of the transversal cross-section represented in B on FIG. 8.

The guiding unit 15 is provided with an internal passage 17 the transversal section of which corresponds to that of the bore or passage defined inside the sheath 49 in order to extend this rigid sheath and act as a housing to the flexible shaft 8. A first portion or input portion 17a of the passage 17 is aligned on the distal terminal portion of the sheath 49 and thus extends, substantially parallel to the longitudinal median axis 7 of the nail 1, when the unit 15 is placed in the recess of the nail, while a second portion or distal portion 17b of the said passage which issues at an outlet orifice 22, forms with the proximal portion 17a a rounded part substantially in a quarter circle which leads the orifice 22 to issue in a manner substantially perpendicular to the wall of the nail 1. The radius of the rounded part of the passage 17 is selected as large as possible in the dimensional limits imposed by the guiding unit 15, so as to limit the wear of the flexible sheath 48 and the flexible rod 51 and to facilitate the transmission of the rotational torque at this rod 51 and the thrust action exerted on the flexible sheath 48. The passage 17 can of course be replaced by an extension of the rigid sheath 49 issuing radially in 22, the sheath 49 being rigidly secured to the guiding unit 15 so that it no longer has to be crossed through by a passage 17 in an arc of a circle. The flexible sheath 48 can be secured in rotation or left free to turn under the effect of the driving in rotation of the flexible rod 51. It is also possible to rotate the flexible sheath 48, either in synchronization with the flexible rod 51, or at a different speed or in the opposite direction for example in order to render rigid the assembly of the flexible sheath 48 and the rod 51 at the output of the orifice 22.

The guiding unit 15 is provided with means for securing or locking position in nail 1. These locking means are again constituted in this embodiment by a blind cylindrical recess 18 extending perpendicular to the axis 7 (with reference to unit 15 introduced in the nail 1) and containing a helical spring 19 coaxial to the said recess which urges, towards the outside of the unit 15, a positioning ball 20 retained in abutment in the recess 18 by an edge 18a but protruding under the action of the spring 19 outside the outlet orifice of the recess. The ball 20 cooperates by snapping with a positioning recess formed in the present example by a hole 21 provided in the wall of the nail 1 in the lobe opposite that which presents the inlet screw holes 2. The site of the positioning hole 21 is selected so that, taking into account the arrangement of the guiding unit, the ball 20 partially penetrates within the hole 21 when the outlet orifice 22 of the passage 17 is aligned with the inlet screw hole 2 of the nail 1. In the embodiment represented, the positioning hole 21 and the outlet screw hole 3 have their respective centers placed on a common generating line in the wall of nail 1. In order to prevent positioning errors, the positioning hole 21 also presents a diameter substantially greater than that of the outlet screw hole 3 and a ball 20 having a relatively great diameter is used that does not risk, during the putting in place of the unit 15, provoking a snapping effect in the screw hole 3, which could be wrongly interpreted as indicating that the unit 15 has reached its locking position in the recess 16 of the nail.

In order to facilitate its manipulation and its positioning, the unit 15 is provided with another rigid tube 23 extending in the same general direction as the sheath 49 and which can be used moreover for observation purposes or locking control of the unit 15.

FIG. 9 shows an intramedullary nail represented in cross-section and the central portion of which has been deleted for enhanced simplicity. In its proximal portion 1a intended to be mounted in the vicinity of the head of a femur, the nail 1 bears two holes 2' and 3' aligned accordingly to an axis 6' inclined at an angle alpha with respect to the longitudinal axis 7 of the nail 1. In a classical manner, the surgeon who has good vision on the proximal portion, can drill transversally in the head of the femur a bore corresponding to holes 2' and 3' in order to place in the cortical of the bone a fixation screw that crosses the holes 2' and 3'.

The distal portion 1b of the nail 1 presents, on the contrary, at least two series of aligned holes for fixation screws crossing through the cortical of the bone according to a direction substantially perpendicular to the axis 7 of the nail 1 and thus to the longitudinal axis of the bone (for example a femur) in the medullary portion of which is implanted the nail 1. The aligned holes are referenced 2, 3 and 2a, 3a on FIG. 9 and to each pair of holes corresponds a hole having a greater diameter 21 and 21a intended to receive a ball 20 for the locking in position of the unit 15.

The putting in place of the distal fixation screws in the aligned holes 2, 3 and 2a, 3a is carried out in the following manner. After the nail 1 is put in place in the medullary recess of the bone such as a femur, guiding unit 15 is introduced by using the tube 23 into the recess 16 of the nail 1. When the engagement of the ball 20 in the positioning hole 21 indicates that the unit 15 has reached its drilling position, in which the orifice 22 of the passage 17 is placed opposite the outlet screw hole 2 of the nail, the flexible rod 51 is turned by means of the motor 14 and the sheath 48 is pushed downwards by means of a plate 48a integral with the sheath 48, so as to press the other end of the sheath 48 in contact with a bearing surface 12a provided to the rear of the bit 12. Under the effect of the thrust of the sheath 48, flexible but quasi rigid in compression, the bit 12 that turns is applied to the adjacent cortical of the bone and drills perpendicular in the internal wall of this bone, a hole or bore that will be perfectly aligned on the screw hole 2.

Thereafter a drilling guide will be put into place, in a manner known per se, through an external route and the surgeon performs a transversal drill crossing through the bone and the holes 2 and 3, which allows utilizing a Kirchner pin crossing through the nail and the two cortical zones of the bone on either side of it, and where necessary, replacing the Kirchner pin by a fixation screw of the nail 1 on the cortical of the bone. Operating procedure is identical for the following holes referenced 2a and 3a by displacing the unit 15 up to the locking of the ball 20 in the large hole 21a.

Of course, the present invention is not limited to the embodiments described and represented herein-above and can be adapted to numerous variants available to the man skilled in the art without departing from the scope and spirit of the invention.

I claim:

1. A boring sensor for use with an intramedullary nail having a wall defining an internal cavity, a screw hole in the wall and a longitudinal axis, for drilling a passage in the cortical wall of a bone, said boring sensor comprising:

a guiding and positioning unit axially movable in said internal cavity of the nail, said unit including a passage extending therethrough, said passage including a first portion substantially parallel with the axis of the nail and a second portion forming an angle with the first portion, said second portion terminating in a distal orifice on a surface of the unit;

a sheath having a proximal end exiting the internal cavity of said nail substantially parallel to the axis of said unit and a distal end connected with said unit and in open communication with said passage, said sheath including a bore extending therethrough from said proximal end to said distal end thereof;

a flexible shaft rotatably positioned in said sheath and said passage, said flexible shaft having a distal end with a boring head thereat and a proximal end adapted to be coupled to a rotary motor; and positioning means on said unit for cooperating with positioning means of said nail to position the distal orifice of said unit in line with said screw hole in the wall of said nail.

2. A boring sensor according to claim 1, wherein the cross-sectional configuration and dimensions of the passage of said guiding and positioning unit is substantially identical to that of the bore of said sheath, and said second portion forms an obtuse angle with said first portion.

3. A boring sensor according to claim 1, wherein said positioning means of said nail includes a positioning recess provided in the wall of the nail at a position determined by the position of said screw hole in the wall of the nail; and said positioning means of said guiding and positioning unit includes a recess, a ball mounted in said recess so as to be movable in a direction substantially transverse to the longitudinal axis of said nail, and spring means for biasing said ball out of said recess, wherein engagement of said ball within the positioning recess in said nail occurs when the distal orifice of the unit is substantially aligned with the screw hole of the nail.

4. A boring sensor according to claim 3, wherein said positioning recess includes a positioning hole extending completely through the wall of the nail.

5. A boring sensor according to claim 1, wherein the sheath includes a substantially rigid wall along a portion of its length.

6. A boring sensor according to claim 5, wherein said sheath includes a substantially rigid wall along its entire length.

7. A boring sensor according to claim 5, wherein said flexible shaft includes a boring head, a rotary flexible rod which presents a high resistance to flexion-rotation stresses, for rotatably driving said boring head, and a flexible sheath, which is at least quasi-rigid in compression, and which is axially movable within said bore of said sheath and said passage of said guiding and positioning unit, in surrounding relation to said rotary flexible rod.

8. A boring sensor according to claim 7, wherein said boring head includes a bearing surface to permit the flexible sheath to push the boring head in order to move the boring head forward during rotation of the boring head by said rotary flexible rod, without exerting any axial force upon said rotary flexible rod.

9. A boring sensor according to claim 7, wherein the boring head is secured to the rotary flexible rod by crimping.

10. A boring sensor according to claim 1, wherein said guiding and positioning unit further includes an axial handling rod extending substantially parallel to the longitudinal axis of the nail to provide a gripping surface that extends beyond a proximal end of said nail for any axial position of the guiding and positioning unit within the nail.

11. Apparatus for drilling a passage in the cortical wall of a bone, comprising: an intramedullary nail having a wall defining an internal cavity, said nail presenting a substantially constant transverse cross-section tubular form and having aligned inlet and outlet screw holes in said wall, said nail having a slightly pointed distal end and a proximal end provided with at least one screw passage in the wall thereof which is inclined with respect to a longitudinal axis of said nail, said nail further including, adjacent said slightly pointed distal end at least two pair of holes transversely aligned with respect to the longitudinal axis of the nail for permitting fixation screws to pass through the nail into the bone and to also define positioning means; and a boring sensor intended to be housed within said intramedullary nail for drilling a passage in the cortical wall of a bone that bears the nail, said boring sensor comprising:

a guiding and positioning unit axially movable in said internal cavity of the nail, said unit including a passage extending therethrough, said passage including a first portion substantially parallel with the axis of the nail and a second portion forming an angle with the first portion, said second portion terminating in a distal orifice on the surface of the unit;

a sheath having a proximal end exiting the internal cavity of said nail substantially parallel to the axis of said unit and a distal end connected with said unit and in open communication with said passage, said sheath including a bore extending therethrough from said proximal end to said distal end thereof, and a portion of said sheath adjacent said guiding and positioning unit including a substantially rigid wall;

a flexible shaft rotatably positioned in said sheath and said passage, said flexible shaft having a distal end with a boring head thereat and a proximal end adapted to be coupled to a rotary motor; and positioning means in said unit for engaging the positioning means of said nail to position said unit in said nail such that the distal orifice of said unit is positioned in line with the screw hole in the wall of said nail.

12. Apparatus according to claim 11, wherein said positioning means in said nail includes a hole which is separate from the at least two pairs of holes; and said positioning means of said guiding and positioning unit includes a recess in said unit, a ball movable in said recess and spring means for biasing said ball out of said recess into engagement with said hole in said nail.

13. Apparatus for drilling a passage in the cortical wall of a bone, comprising:

an intramedullary nail having a wall defining an internal cavity, said wall including a non-circular cross-sectional configuration which is constant along a major portion of the length thereof, said wall including at least one inlet screw hole and at least one outlet screw hole in a distal portion of said wall, said at least one inlet screw hole and said at least one outlet screw hole aligned along a common axis which is inclined with respect to a longitudinal axis of said nail at a predetermined angle;

a guiding and positioning unit axially movable in said internal cavity of the nail, said unit including a passage extending therethrough, said passage including a first portion substantially parallel with the axis of the nail and a second portion extending at said predetermined angle with respect to said first portion, said second portion terminating in a distal orifice on the surface of the unit;

a sheath having a proximal end exiting the internal cavity of said nail substantially parallel to the axis of said nail and a distal end connected with said unit and in open communication with said passage, said sheath including a bore extending therethrough from said proximal end to said distal end thereof;

a flexible shaft rotatably positioned in said sheath and said passage, said flexible shaft having a distal end with a boring head thereat and a proximal end adapted to be coupled to a rotary motor; and positioning means in said unit for engaging with the positioning means in said nail such that the distal orifice of said unit is positioned in line with said screw holes in the wall of said nail, said positioning means of said nail including a positioning recess and said positioning means of said unit including a recess in said unit, a ball movable in said recess and spring means for biasing said ball out of said recess into engagement with said positioning recess.

14. Apparatus according to claim 13, wherein said positioning recess includes a positioning hole extending entirely through the wall of the nail.

15. Apparatus according to claim 14, wherein said positioning hole has an axis situated in a common plane with the common axis of said inlet and outlet of said screw holes.

16. Apparatus according to claim 15, wherein said positioning hole has a diameter substantially larger than that of said outlet screw hole.

17. Apparatus according to claim 16, wherein said positioning hole has an axis situated in a plane angularly shifted with respect to a plane containing the common axis of the inlet and outlet screw holes.

18. Apparatus according to claim 13, wherein said nail has a transverse cross-section provided with a plurality of lobes, and said guiding and positioning unit ha an external outline matching at least that of one of said lobes.

19. Apparatus according to claim 18, wherein said nail has three said lobes and said guiding and positioning unit includes an external outline matching two of said lobes.

* * * * *